United States Patent
Oefelein et al.

(10) Patent No.: US 10,383,942 B2
(45) Date of Patent: Aug. 20, 2019

(54) RETINOID TOPICAL COMPOSITIONS AND METHODS FOR TREATING SKIN CONDITIONS

(71) Applicant: Allergan, Inc., Irvine, CA (US)

(72) Inventors: Michael G. Oefelein, Tustin, CA (US); Jeffrey R. Ehrhardt, San Clemente, CA (US); Gurpreet Ahluwalia, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/804,090

(22) Filed: Jul. 20, 2015

(65) Prior Publication Data

US 2015/0320732 A1    Nov. 12, 2015

Related U.S. Application Data

(63) Continuation of application No. 13/530,468, filed on Jun. 22, 2012, now abandoned.

(60) Provisional application No. 61/503,210, filed on Jun. 30, 2011.

(51) Int. Cl.

| | |
|---|---|
| *A61K 31/4436* | (2006.01) |
| *A61K 31/136* | (2006.01) |
| *A61K 9/00* | (2006.01) |
| *A61K 45/06* | (2006.01) |
| *A61K 31/327* | (2006.01) |
| *A61K 31/7056* | (2006.01) |
| *A61Q 19/00* | (2006.01) |
| *A61K 8/49* | (2006.01) |

(52) U.S. Cl.
CPC ............ *A61K 45/06* (2013.01); *A61K 8/4926* (2013.01); *A61K 9/0014* (2013.01); *A61K 31/136* (2013.01); *A61K 31/327* (2013.01); *A61K 31/4436* (2013.01); *A61K 31/7056* (2013.01); *A61Q 19/00* (2013.01)

(58) Field of Classification Search
CPC ............ A61K 31/4436; A61K 31/136; A61K 9/0014; A61K 31/327; A61K 31/7056; A61K 45/06; A61K 2300/00; A61Q 19/00

USPC ......................................................... 514/337
See application file for complete search history.

(56) References Cited

U.S. PATENT DOCUMENTS

| | | | |
|---|---|---|---|
| 6,060,085 A | 5/2000 | Osborne | |
| 7,141,237 B2 | 11/2006 | Abram et al. | |
| 2007/0003585 A1 | 1/2007 | Clark et al. | |
| 2009/0226380 A1 | 9/2009 | Clark | |
| 2010/0221194 A1 | 9/2010 | Loupenok | |

FOREIGN PATENT DOCUMENTS

| | | |
|---|---|---|
| WO | WO2004-064803 | 8/2004 |
| WO | WO2011-014627 | 2/2011 |

OTHER PUBLICATIONS

Glossary of medical education terms, Institute of International Medical Education. http://www.iime.org/glossary.htm Accessed in Mar. 2013.*
Sandoval et al. Current and future evidence-based acne treatment: a review. Expert Opin. Pharmacother. (2014) 15(2):173-192.*
Fleischer et al. Dapsone Gel 5% in Combination With Adapalene Gel 0.1%, Benzoyl Peroxide Gel 4% or Moisturizer for the Treatment of Acne Vulgaris: A 12-Week, Randomized, Double-Blind Study. J Drugs Dermatol 9:33-40, Jan. 2010.*
Allergan, Inc., Aczone (dapsone) Gel 5%, Highlights of Prescribing Information, Mar. 2009, 11 pp., Allergan, Inc., Irvine, CA, US.
International Search Report and the Written Opinion, International Application No. PCT/US2012/043833, International Filing Date Jun. 22, 2012, dated Aug. 8, 2012.
Tanghetti, Emil et al, Unexpected Benefits of Topical Dapsone or Clindamycin/Benzoyl Peroxide in Combination With Tazarotene in Treatment of Comedonal Acne, Journal of the American Academy of Dermatology, Feb. 2011, P703-AB13, 64(2).

* cited by examiner

*Primary Examiner* — Yih-Horng Shiao
(74) *Attorney, Agent, or Firm* — Laura L. Wine

(57) ABSTRACT

A topical pharmaceutical composition comprising tazarotene and one or more of an anti-inflammatory or antibacterial agent. Also provided is a method for treating skin conditions, such as acne utilizing the above topical pharmaceutical composition.

4 Claims, No Drawings

RETINOID TOPICAL COMPOSITIONS AND METHODS FOR TREATING SKIN CONDITIONS

CROSS-REFERENCE TO RELATED APPLICATION

This application is a continuation of copending U.S. patent application Ser. No. 13/530,468, filed on Jun. 22, 2012, which claims the benefit of U.S. provisional application No. 61/503,210, filed on Jun. 30, 2011, the entire disclosure of both applications are incorporated herein by this specific reference.

BACKGROUND

Retinoids are biologically active chemical compounds related to Vitamin A. Retinoids are used, among other areas, in the fields of dermatology and cosmetology. A variety of non-retinoid compounds are known that exert anti-inflammatory action, anti-microbial action, and other actions, such as immunomodulation and an ability to increase skin peeling, when applied topically. Such non-retinoid active agents include antibiotics and other anti-bacterial compounds, steroids, non-steroid anti-inflammatory drugs (NSAIDs), as well as other anti-inflammatory agents that are not conventionally categorized as steroids or NSAIDs. The antibiotics used in the topical compositions include tetracycline, erythromycin, and clindamycin. Benzoyl peroxide, which exerts its antibacterial action via its potent oxidizing properties and stimulates skin peeling, is another common non-retinoid active agent included in topical formulations. Dapsone, a compound known to have anti-inflammatory, anti-bacterial and immunomodulatory effects, is one more example of a non-retinoid active agent used in topical formulations.

Acne is a group of common skin conditions characterized by the so-called "acneiform" or acne-like skin eruptions, which can be contaminated with bacteria, such as *Propionibacterium acnes*, and can also be marked by inflammation. Acne tends to occur in the areas of skin where the sebaceous glands are most active, such as the face. Acne is associated with psychological trauma, and, if left untreated, can lead to scar formation and disfigurement.

Classification and the diagnosis of various acne conditions can be complex, and even contradictory. Given this complexity and unpredictability, medication and other therapies, are often developed on a trial-and-error basis in order to determine the most effective course of treatment for a particular patient. The outcome of any particular acne treatment regimen greatly varies from patient to patient, as well as throughout treatment of a particular patient. In addition to the complexity and variability of acne conditions, treatment efficacy can be greatly affected by a patient's compliance with the treatment regimen. Patient compliance during acne treatment may be influenced by side effects, which, for topical mediations, commonly include redness, itching, and skin peeling. The complexity of the drug regiment can also negatively affect patient compliance, particularly where two or more different topical medications are prescribed simultaneously. Another factor that negatively affects patient compliance is the cost of a drug regiment, which is considerably higher when multiple medications are prescribed. In some countries, acne is considered a cosmetic problem, and acne treatments are not covered by insurance plans, thus further increasing patient's treatment costs. Certain compositions for treatment of acne are available. Many of the available compositions include one active agent known to have anti-acne activity. Stability of compositions with multiple anti-acne agents can be problematic. Also, these compositions can be difficult to manufacture.

The problems described above are not confined to the treatment or acne, but are also applicable to a variety of other skin conditions, including, but not limited, to conditions or classes of conditions with complex or unknown etiology and that are difficult to classify or diagnose, in which, nevertheless, topical application of agents are known to be effective at least in some cases. Examples of such conditions or classes of conditions include psoriasis, rosacea and ichthyosis.

Accordingly, there is a continuing need for compositions and methods used in a treatment of a variety of skin conditions, such as acne, in which topical application is potentially effective. In particular, topical compositions comprising retinoids and methods are needed that would, for example, exhibit improved effectiveness, reduced side effects, or both, when used in a particular patient with a skin condition. Such improved topical compositions comprising retinoids and methods of their uses are also needed to improve treatment of patients with acne or suspected acne. The compositions and methods provided herein address these and other needs in the art.

SUMMARY

Embodiments of the invention described herein include topical compositions including a retinoid (e.g. topically active retinoid) and a topically active non-retinoid agent and methods for treating skin conditions including applying a retinoid (e.g. a topically active retinoid) and a topically active non-retinoid agent to a skin of a patient.

A topically active non-retinoid agent employed in the compositions, products and methods according to the embodiments provided herein is a non-retinoid compound having at least anti-inflammatory properties or anti-bacterial properties, when applied topically. Certain embodiments of the compositions, products and methods described herein are useful for topical treatment of skin diseases or conditions that involve inflammation, acne or acneiform symptoms. Accordingly, topical compositions and products described herein are formulated for topical administration.

Embodiments of combination topical compositions provided herein include at least one topically active retinoid in an effective amount and at least one topically active non-retinoid agent in an effective amount. Combination products for topical application according to some embodiments of the present invention include a composition including a topically active retinoid in an effective amount, and a composition comprising a topically active non-retinoid agent in an effective amount.

Some embodiments of methods of treating skin conditions described herein involve topical application of a combination composition to a skin of patient or application of a combination product to a skin of a patient. Some other embodiments of methods of treatment of skin conditions described herein involve topical application to a skin of a patient of a first composition including a retinoid and topical application of a second composition including one or more topically active non-retinoid agent. Tazarotene is an example of a topically active retinoid used in the compositions, products and methods provided herein. Examples of topically active non-retinoid agents used in the methods, products and compositions according to the embodiments of the present invention are dapsone, benzoyl peroxide, and topically active antibiotics, such as clindamycin.

Compositions, products and methods according to embodiments of the invention described herein are useful, inter alia, for treating a variety of skin conditions in which both topical application of retinoids and topical application of anti-inflammatory, anti-bacterial or other non-retinoid agents is potentially effective. Compositions, products and methods according to certain embodiments of the invention described herein exhibit improved efficacy, reduced side effects, or both, as compared to conventional compositions, products and methods, when used for treatment of a skin condition in a patient. Compositions, products and methods described herein exhibit unexpected advantages as compared to conventional compositions, products and methods, when incorporated into treatment regimens of patients having acne. Unexpected advantages of the compositions, products and methods according to the embodiments of the invention described herein may include one or more of improved efficacy, lowered side effects, improved patient compliance and lowered cost of treatment, when the compositions, products and methods are used in the treatment of acne. Certain embodiments of the compositions and products described herein may also display unexpectedly improved stability, increased ease of production, storage and/or use, as compared to conventional compositions and products.

DETAILED DESCRIPTION

Embodiments of the present invention include compositions and products for treatment of skin conditions and methods of treating skin conditions. The term "skin condition" as used herein encompasses human and animal conditions, disorders, or diseases affecting skin, in which topical application of retinoids is potentially effective. Such skin conditions include, but are not limited to, conditions involving skin inflammation, conditions involving sebaceous glands and hair follicles, conditions characterized by acneiform symptoms, and conditions involving skin dryness, skin thickening, skin scaling or skin flaking. Skin conditions encompassed by the embodiments of the compositions, products and methods described herein include, but are not limited to, acne, rosacea, folliculitis, perioral dermatitis, photodamage, skin aging, psoriasis, ichthyosis, atopic dermatitis, treatment of chronic wounds, bed sores, keratosis pilaris, scars, including surgical and acne scars, sebaceous cysts, inflammatory dermatoses, post inflammatory hyperpigmentation, eczema, xerosis, pruritis, pruritus, lichen planus, nodular prurigo, eczema, and miliaria.

The term "acne," as used herein, encompasses skin conditions involving acneiform or acne-like symptoms. For example, a skin condition characterized by follicular eruptions, such as papules and pustules resembling acne, can be categorized as acne. It is to be understood that the term "acne" is not to be limited to diseases and conditions characterized by papules and pustules, but can be characterized by a variety of symptoms. It is also to be understood a particular patient having acne can be in remission, or the patient's acne can be controlled by continuing treatments, and therefore the patient can exhibit reduced symptoms or be asymptomatic. Nevertheless, continuing treatment of acne can be recommended in such a patient in order to reduce the probability of the return of the acne symptoms.

Symptoms of acne or acne-like conditions include, but are not limited to, the appearance of various skin lesions. The term "lesion" is generally used to denote an infected or diseased patch of skin. A lesion can involve an infected sebaceous gland. Some lesions are more severe than others. Examples of skin lesions are comedones, macules, papules, pustules, nodules and cysts. The term "comedo" (plural "comedones") is used to describe a sebaceous follicle plugged with dirt, other cells, tiny hairs, or bacteria. Comedones include the so-called "blackheads," which can also refer to as "open comedones," which have a spot or a surface that appears black. Comedones also include slightly inflamed, skin colored bumps, as well as "whiteheads," which have a spot or a surface that appears white. The term "macule" generally refers to a flat spot or area of the skin with a changed color, such as a red spot. The term "pustule" is generally used to refer to an inflamed, pus-filled lesion, or a small inflamed elevation of the skin that is filled with pus. The term "papule" is generally used to refer to a small, solid, usually inflammatory elevation of the skin that does not contain pus. The term "nodule" is generally used to refer to an elevation of a skin that is similar to a papule but is white and dome-shaped. Colloquially, a papule, a pustule or a nodule can be referred to as "a pimple" or "a zit." The term "cyst" generally refers to an abnormal membranous sac containing a liquid or semi-liquid substance containing white blood cells, dead cells, and bacteria. Cysts can be painful and extend to deeper layers of skin.

In dermatological science and dermatological and cosmetology practice, acne can be classified or categorized into one or more types or categories, according to one or more lines of categorization, such as a predominantly observed type of symptoms, severity of condition or predominant localization. It is to be understood that classification of acne into one of the subtypes does not mean that the characteristics of the classified condition are limited to the symptoms associated with the specific type.

Comedonal acne is characterized by the appearance of non-inflammatory lesions, such as blackheads and whiteheads. Localized cystic acne is characterized by appearance of a few cysts on face, chest and back. Diffuse cystic acne is characterized by the appearance of cysts on wide areas of face, chest and back. Nodular acne is characterized by the appearance of nodules. Nodulocystic acne is characterized by appearance of nodules and cysts. Acne vulgaris is a common form of acne characterized by the appearance of several types of lesion, which may appear together or separately. Individual acne lesions usually last less than two weeks but the deeper papules and nodules may persist for months. Acne vulgaris commonly affects adolescents, but it may also appear, persist or become more severe in adulthood. Acne vulgaris may occur on the face, chest, back and sometimes even more extensively.

Depending on a severity, acne can be mild, moderate or severe. Mild acne is generally categorized by the appearance of with blackheads and whitehead, but can also include papules and pustules. Moderate acne is generally characterized by appearance of more painful, deep-rooted inflamed lesions, which can result in scarring. Severe acne is characterized by the appearance of deep-rooted inflammatory lesions, including cysts and nodules which are painful and can produce scarring. Acne conglobata is a category of acne characterized by highly inflammatory cysts that communicate under the skin with abscesses and burrowing sinus tracts.

Some other skin conditions exhibiting acne-like symptoms and intended to be included in the scope of some of the embodiments of the present invention are discussed below. Pyoderma faciale, also known as rosacea fulminans, is a condition that appears in females and is characterized by abrupt appearance of inflamed cysts and nodules localized on the face. Rosacea, which can be referred to as acne rosacea, is a condition that can affects both the skin and the eyes and is characterized by redness, bumps, pimples, and, in advanced stages, thickened skin on the nose. In some classification systems, rosacea and acne are considered as separate conditions. Rosacea usually occurs on the face, although the neck and upper chest are also sometimes involved. A mild degree of eye (ocular) involvement occurs in more than fifty percent of people with rosacea. Perioral dermatitis is characterized by the appearance of small tiny papules, pustules, red bumps and scaling with intense itching. It is usually localized to the surrounding area of the mouth and on the chin, or extends to involve the eyelids and the forehead. Gram-negative folliculitis is a bacterial infection characterized by the appearance of pustules and cysts, possibly occurring as a complication resulting from a long term antibiotic treatment of acne vulgaris.

As used herein, the terms "treatment" or "treating" in reference to a skin condition generally mean "having positive effect on a skin condition" and encompass alleviation of at least one symptom of a skin condition, a reduction in the severity of the skin conditions, or delay, prevention, or inhibition of the progression of the skin condition. Treatment need not mean that the condition is totally cured. A composition or a product useful for treatment of a skin condition, or a method of treating a skin condition, needs only to reduce the severity of a skin condition, reduce the severity of symptoms associated therewith, provide improvement to a patient's quality of life, or delay, prevent, or inhibit the onset of symptoms of a skin condition.

As used herein, the terms "application," "apply," and "applying" used in reference a topical composition product or method of using a composition or a product, refer or to any manner of administering a topical composition or a product a skin of a patient which, in medical or cosmetology practice, delivers the composition or the product to patient's skin surface. Smearing, rubbing, spreading, spraying a topical composition, with or without the aid of suitable devices, on a patient's skin are all included within the scope of the term "application," as used herein. The term "topical" or "topically" in reference to administration or application of a composition or a product refers to epicutaneous application administration or application, or administration onto skin. The term "topically active agent" as used herein refers to a compound that is effective in a treatment of a skin condition when administered topically. It is to be understood that topically active agent can have a local or a systemic effect, or both, when administered topically. The term "topical," when used in reference to a composition or a product refers to a composition or a product formulated for topical application. As used herein, the terms "effective amount" refers to an amount of an active agent effective to treat a skin condition, including a range of effects, from a detectable local improvement in an area of topical application to substantial relief of symptoms. Effective amounts of a topically active agent will vary with the particular condition or conditions being treated, the severity of the condition, the duration of the treatment, the specific components of the composition being used, and other factors.

Topical compositions and products according to embodiments of the present invention are formulated to be suitable for topical administration and include, but are not limited to solutions, gels, creams, ointments, foams, emulsions, pastes, balms, sprays, suspensions, ointments films, and facial/skin peels. Topical compositions and products according to embodiments of the present invention include one or more active agent and at least one or more acceptable excipients or carriers. It is to be understood that any of the components of the topical compositions or products referred to as excipients or carriers, or inactive agents, nevertheless can improve effectiveness of reduce side effects of the topical composition, and can also have independent positive effects on a patient's skin, such as a moisturizing effect.

Topical compositions and products according to embodiments of the present invention can be formulated as emulsions, such as oil-in-water or water-in-oil systems. Accordingly, topical compositions and products may comprise an emulsifier. Non-limiting examples of emulsifiers include glycol esters, fatty acids, fatty alcohols, fatty acid glycol esters, fatty esters, fatty ethers, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, derivatives thereof, and mixtures thereof. Topical compositions and products according to embodiments of the present invention can be formulated as creams, which can be semi-solid emulsions of oil and water, and lotions, including suspensions of powdered material in water or alcohol base and water-based emulsions. Topical compositions and products according to embodiments of the present invention can also be formulated as ointments, which are oleaginous and contain little if any water.

Topical compositions and products according to embodiments of the present invention can contain a gelling agent, a thickener, or both. Suitable gelling agents and include aqueous thickening agents, such as neutral, anionic, and cationic polymers, and mixtures thereof. Exemplary polymers which may be useful in the instant compositions include carboxy vinyl polymers, such as carboxypolymethylene, and carbomers. Other, non-limiting example of suitable thickeners useful herein include cellulosic polymers, such as gum arabic, gum acacia, gum tragacanth, locust bean gum, guar gum, hydroxypropyl guar, xanthan gum, cellulose gum, sclerotium gum, carrageenan gum, karaya gum, cellulose gum, rosin, methylcellulose, hydroxyethylcellulose, hydroxypropylcellulose, hydroxymethylcellulose, hydroxypropylmethylcellulose, methylhydroxyethylcellulose, cetyl hydroxyethylcellulose, carboxymethylcellulose, corn starch, hydroxypropyl starch phosphate, distarch phosphate, distarch dimethylene urea, aluminum starch octenyl succinate, maltodextrin, dextran, poly(acrylamide), PEG-150 distearate, PEG-150/decyl alcohol/SMDI copolymer, PEG-150/stearyl alcohol/SMDI copolymer, PEG-180/Laureth-50/TMMG copolymer, Polyether 1, acrylic acid/acrylamidomethyl propane sulfonic acid copolymer, acrylate/C10-30 alkyl acrylate crosspolymer, acrylate/beheneth-25 methacrylate copolymer, acrylate/steareth-20 methacrylate copolymer, acrylate/steareth-20 copolymer, acrylate/VA crosspolymer, acrylic acid/acrylonitrogen copolymer, ammonium acryloyldimethyltaurate/beheneth-25 methacrylate copolymer, ammonium acryloyldimethyltaurate/VP copolymer, caprylic/capric triglyceride (and) sodium acrylate copolymer, PVM/MA decadiene crosspolymer, alginic acid, propylene glycol alginate, dimethicone, silica dimethyl silylate, a dimethylacrylamide/acrylic acid/polystyrene ethyl methacrylate copolymer, derivatives thereof, and mixtures thereof.

Any other non-toxic, inert and effective carrier or excipient may be used to formulate topical compositions and products according to embodiments of the present invention. Examples of such useful pharmaceutically acceptable excipients, carriers and diluents include water, physiological saline, Ringer's solution, dextrose solution, Hank's solution, DMSO, a carbomer, a polyacrylic polymer, glycerin, sodium hydroxide, sodium thiosulfate, propyl gallate, an alkyl paraben, purified water, and mixtures thereof. Other ingredients, which may optionally be included into the topical compositions and products according to embodiments of the present invention, include humectants, such as propylene glycol; solvents, such as alcohols, sun filters, such as titanium dioxide, zinc oxide, and calcium carbonate; and anti-microbial preservatives, such as methylparaben and propylparaben. An organic or inorganic base may also be included, such as sodium hydroxide, which is used to adjust the pH of the initial components and the final product. Generally, dermatologically acceptable excipients commonly known in the fields of dermatology and cosmetology as useful in topical compositions, and any non-toxic, inert, and effective topical carriers, are contemplated as useful in the compositions and products according to the embodiments of the present invention.

As used herein, the phrase "pharmaceutically acceptable salts" refers to salts of the active compound(s) which possess the same pharmacological activity as the active compound(s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfuric acid, boric acid, butyric acid, camphoric acid, camphorsulfonic acid, carbonic acid, citric acid, cyclopentanepropionic acid, digluconic acid, dodecylsulfuric acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfuric acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylenesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, naturally and synthetically derived amino acids. Non-limiting examples of base salts include ammonium salts; alkali metal salts, such as sodium and potassium salts; alkaline earth metal salts, such as calcium and magnesium salts; salts with organic bases, such as dicyclohexylamine salts; methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others.

The compositions according to some embodiments of the present invention are topical combination compositions comprising a topically active retinoid and a topically active non-retinoid agent. More specifically, the topical combination compositions described herein are pharmaceutical compositions formulated for topical application, which comprise at least one topically active retinoid in an effective amount and at least one topically active non-retinoid agent in an effective amount.

The products according to some embodiments of the present invention are topical combination products comprising a first composition comprising a topically active retinoid and a second composition topically active non-retinoid agent. In some embodiments, the first composition comprises a topically active retinoid in an effective amount. Some embodiments can include the second composition in an effective amount. In some other embodiments of the combination product, a topically active retinoid is found in an effective amount in the product, but may not be found in an effective amount in the first composition. The first composition can include an amount of a topically active retinoid that is lower or higher than an effective amount. Similarly, embodiments of the products are envisioned, in which a topically active non-retinoid agent may be found in an effective amount in the product, but may not be found in an effective amount in the second composition. The first composition can include an amount of a topically active non-retinoid agent that is lower or higher than an effective amount.

In some embodiments, both a first and a second composition included into a topical combination product are topical compositions, or compositions formulated for topical application. In some other embodiments, however, a first composition, a second composition, or both, do not have to be formulated for topical application, but the topical combination product is suitable for topical application after one or more manipulations are performed with a first composition, a second composition, or both. For example, an embodiment of a combination product may comprise a first topical composition and a second composition, wherein the second composition is not formulated for topical application. The second composition, however, may be incorporated into the first composition, for example, by mixing, prior to application of the topical product. In another exemplary embodiment of a combination product, the first and the second composition formulations may be packaged separately, but under a single outside packaging container such that when dispensed the two compositions exude at the same time, and thus providing a simple and convenient means of application of the combination product. In another exemplary embodiment of a combination product, a combination product comprises a first composition not formulated for topical administration, a second composition not formulated for topical administration, and a product base formulated for topical administration. The first composition and the second compositions are incorporated into the product base prior to administration.

A topical combination product according to some embodiments of the present invention can include at least one device or an apparatus suitable for packaging, storage or application of the first composition, the first composition, or both. One example of such a device or apparatus is a dual chamber device, such as a dual chamber pen or tube, with the first composition packaged in a first chamber and the second composition packaged in a second chamber. The two compositions are applied to a skin of a patient substantially simultaneously when the dual chamber device is manipulated to push out the first composition and the first composition out of the device's respective chamber. Another example of such a device or apparatus is a triple chamber device, such as a triple chamber pen or tube, with the first composition packaged in a first chamber and the second composition packaged in a second chamber. The two compositions are mixed in a third chamber before application to a skin of a patient, when the triple chamber device is manipulated to push out the first composition and the first composition out of the device's first and second chambers into the third chamber. In some embodiments of the combination products, incorporating the device or the apparatus allows for separate formulation and storage of the first composition and the second composition, thus improving their stability. Incorporating the device or the apparatus into a combination product can also simplify the storage and the use of the product, thus lowering its costs and improving patient compliance.

A retinoid is a chemical compound related chemically to vitamin A. A non-retinoid agent according to embodiments of the present invention is a chemical compound not related chemically to vitamin A. It is to be understood that a topically active non-retinoid agent included into the topical combination compositions described herein possesses non-inflammatory or anti-bacterial properties, or both, when applied topically, and can possess other properties that are useful for treatment to skin conditions discussed elsewhere in this document. It is also to be understood that a topically active retinoid or a topically active non-retinoid agent can exert its action on a skin condition by a variety of mechanisms, and embodiments of the methods, compositions and products described herein are not limited or confined to any particular mechanism of action of a retinoid or a non-retinoid agent.

Tazarotene is an example of a topically active retinoid used in compositions, products and methods according to the embodiments of the present invention. Examples of non-retinoid topically active agents suitable for the compositions, products and methods according to the embodiments of the present invention are dapsone, benzoyl peroxide, and topically active antibiotics, such as clindamycin. It is also to be understood that pharmaceutically acceptable salts of topically active derivatives of retinoid or non-retinoid agents can also be included in the topical combination compositions according to the embodiments of the present invention.

Tazarotene is a topically active retinoid having a systematic name of ethyl 6-[2-(4,4-dimethyl-3,4-dihydro-2H-1-benzothiopyran-6-yl)ethynyl]pyridine-3-carboxylate, which is typically formulated old as a topical cream or gel. Compositions and products according to some embodiments of the present invention comprise tazarotene in an effective amount, for example, at a concentration from 0.05% to 0.3% w/w. In particular, tazarotene concentrations of 0.05%, 0.08%, 0.10%, 0.13%, 0.15%, 0.18%, 0.20%, 0.23%, 0.25%, 0.28% and 0.30% w/w are employed in the topical combination compositions and topical products described herein.

Dapsone is diamino-diphenyl sulfone with a systematic name of 4-[(4-aminobenzene)sulfonyl]aniline, which is marketed as a commercial product Aczone®, and is a topically active non-retinoid agent. At the biochemical and molecular level, dapsone exhibits an anti-inflammatory activity, although dapsone's mechanism of action is not entirely understood. Dapsone is known to suppress neutrophil recruitment and local production of their toxic products by inhibiting neutrophil chemotaxis and reducing generation of oxygen free radicals. It is also known to inhibit release of lysosomal enzymes and to reduce release and inflammatory effects of prostaglandins and leukotrienes. These effects result in reduction of inflammatory acne lesions. In addition to its anti-inflammatory activity, dapsone also has anti-bacterial properties and is effective against P. acnes. Compositions and products according to some embodiments of the present invention comprise dapsone in an effective amount, for example, at a concentration from 0.5% to 10% w/w. In particular, dapsone concentrations of 0.50%, 1.00%, 1.50%, 2.00%, 2.50%, 3.00%, 3.50%, 4.00%, 4.50%, 5.00%, 5.50%, 6.00%, 6.50%, 7.0%, 7.50%, 8.00%, 8.50%, 8.75%, 9.00%, 9.25%, 9.50%, 9.75%, 10.00%, 10.50%, 10.75%, 11.00%, 11.50%, 11.75%, 12.00%, 12.50%, 12.75%, 13.00%, 13.50%, 13.75%, 14.00%, 14.50%, 14.75%, and 15.00% w/w are employed in the topical combination compositions and topical products described herein.

Benzoyl peroxide, or dibenzoyl peroxide, is a non-retinoid topically active agent, which consists of two benzoyl groups bridged by a peroxide link. When applied topically in an effective amount, benzoyl peroxide works as a peeling agent, increasing skin turnover and clearing pores, thus reducing the bacterial count. It is also known to act directly as an antimicrobial agent. Compositions and products according to some embodiments of the present invention comprise benzoyl peroxide in an effective amount, for example, at a concentration from 0.5% to 10% w/w. In particular, benzoyl peroxide concentrations of 0.50%, 1.00%, 1.50%, 2.00%, 2.50%, 3.00%, 3.50%, 4.00%, 4.50%, 5.00%, 5.50%, 6.00%, 6.50%, 7.0%, 7.50%, 8.00%, 8.50%, 8.75%, 9.00%, 9.25%, 9.50%, 9.75%, 10.00% w/w are employed in the topical combination compositions and topical products described herein.

Clindamycin is a lincosamide antibiotic with a systematic name of methyl 7-chloro-6,7,8-trideoxy-6-{[(4R)-1-methyl-4-propyl-L-prolyl]amino}-1-thio-L-threo-α-D-galacto-octopyranoside. It is usually used to treat infections with anaerobic bacteria and is a topically active agent commonly used in treatment for acne. Compositions and products according to some embodiments of the present invention comprise clindamycin in an effective amount, for example, at a concentration from 0.5 to 2% w/w. In particular, clindamycin concentrations of 0.50%, 0.75%, 1.00%, 1.25%, 1.50%, 1.75%, 2.00%, 2.25%, 2.50%, 2.75% and 3.00% w/w are employed in the topical combination compositions and topical products described herein.

Table 1 describes various examples of combinations of effective amounts of tazarotene and dapsone useful in the methods, products and compositions provided herein. In particular, Table 1 provides 253 different combinations of concentrations of tazarotene, as shown in the first column labeled "Tazarotene", and dapsone, as shown in the first row labeled "Dapsone." Specific concentrations of tazarotene and dapsone for each of the combinations described in Table 1 and numbered from 1 to 253 are shown, respectively, in the cells in the first column and in the first row, which correspond to the numbered cell. Topical combination compositions and products are provided which comprise effective amounts of tazarotene and dapsone. Methods of treating skin conditions are provided which use effective amounts of tazarotene and dapsone. Some of the compositions, products and methods provided herein possess unexpectedly advantageous properties in comparison with the conventional topical compositions, products, and methods of treating skin conditions.

Table 2 describes examples of combinations of effective amounts of benzoyl peroxide, as shown in the first row labeled "Benzoyl peroxide," and clindamycin, shown in in the first column labeled "Clindamycin," that are useful in the compositions, products and methods provided herein. Specific concentrations of clindamycin and benzoyl peroxide for each of the combinations described in Table 2, labeled by numbers from 1001 through 1287, are shown, respectively, in a corresponding cell in the first column and in the first row for each numbered cell. Compositions and products are provided herein comprising tazarotene at each of the concentrations of 0.05%, 0.08%, 0.10%, 0.13%, 0.15%, 0.18%, 0.20%, 0.23%, 0.25%, 0.28% and 0.30% w/w, and further comprising clindamycin, benzoyl peroxide, or both, at concentrations set forth in combinations 1001-1287 shown in Table 2. Thus, 3157 individual combination products of tazarotene, clindamycin and benzoyl peroxide are specifically disclosed herein and are useful in the compositions, products and methods provided herein.

Compositions and products are also provided which comprise effective amounts of tazarotene and dapsone, as shown in Table 1, one or both benzoyl peroxide and clindamycin at the concentrations shown in Table 2, as well as combination 1001-1287 shown in Table 2 with tazarotene at each of the concentrations of 0.05%, 0.08%, 0.10%, 0.13%, 0.15%, 0.18%, 0.20%, 0.23%, 0.25%, 0.28% and 0.30% w/w. In some embodiments, the compositions and products provided herein possess unexpectedly advantageous properties in comparison with the conventional topical compositions and products.

Methods of treating a skin condition are provided, including methods of treating acne. Some embodiments of the methods provided herein comprise applying a topical combination composition described herein to a skin of a patient having the skin condition, such as acne. Other embodiments of the methods provided herein comprise applying a topical combination product described herein to a skin of a patient having the skin condition, such as acne. Some other embodiments of the methods provided herein comprise applying, within a specified period of time, a composition comprising tazarotene and one or more or more compositions comprising at least one of dapsone, benzoyl peroxide and clindamycin, to a skin of a patient having the skin condition. One embodiment of a method of treating a skin condition comprises applying to a skin of a patient having a skin condition a composition comprising tazarotene at each of the concentrations of 0.05%, 0.08%, 0.10%, 0.13%, 0.15%, 0.18%, 0.20%, 0.23%, 0.25%, 0.28% and 0.30% w/w, and applying to the skin of the patient having the skin condition a composition comprising clindamycin, benzoyl peroxide, or both, at concentrations 1001-1287 shown in Table 2. Methods of treating skin conditions are also provided comprising applying to a skin of a patient of a composition comprising effective amounts of tazarotene and dapsone, as shown in Table 1, and applying to the skin of the patient of a composition comprising one or both benzoyl peroxide and clindamycin at the concentrations shown in Table 2.

Unexpected advantages of the compositions, products and methods according to the embodiments of the invention described herein may include one or more of improved efficacy, lowered side effects, improved patient compliance and lowered cost of treatment. An unexpended advantage of the compositions, products and methods according to some of the embodiments of the present invention is synergism between a retinoid and one or more non-retinoid agents used in a compositions, products and methods according to the embodiments of the present invention. For example, when compositions, products and methods according to some embodiments of the present invention are used for treatment of patients having acne, treatment outcomes are higher than expected based on the treatment outcomes observed separately for compositions, products or methods using only a retinoid agent or only a non-retinoid agent. Certain embodiments of the topical compositions and products described herein also display improved stability, lowered costs, and are easier to produce, store and use, as compared to conventional compositions and products. Improved patient compliance and/or improved treatment outcomes may also be observed when some embodiments of the topical compositions, products and methods described herein are used for treatment to skin conditions, such as acne, as compared to the use of conventional compositions, products and methods. In some instances, any or all improvements observed for the compositions, products and methods are unexpected, based on the information, such as scientific or clinical data, available for the conventional compositions, products and methods.

TABLE 1

EFFECTIVE AMOUNTS OF TAZAROTENE AND DAPSONE

| Tazarotene | Dapsone (w/w) | | | | | | | | | | | |
|---|---|---|---|---|---|---|---|---|---|---|---|---|
| (w/w) | 0.50% | 1.00% | 1.50% | 2.00% | 2.50% | 3.00% | 3.50% | 4.00% | 4.50% | 5.00% | 5.50% | 6.00% |
| 0.05% | 1 | 12 | 23 | 34 | 45 | 56 | 67 | 78 | 89 | 100 | 111 | 122 |
| 0.08% | 2 | 13 | 24 | 35 | 46 | 57 | 68 | 79 | 90 | 101 | 112 | 123 |
| 0.10% | 3 | 14 | 25 | 36 | 47 | 58 | 69 | 80 | 91 | 102 | 113 | 124 |
| 0.13% | 4 | 15 | 26 | 37 | 48 | 59 | 70 | 81 | 92 | 103 | 114 | 125 |
| 0.15% | 5 | 16 | 27 | 38 | 49 | 60 | 71 | 82 | 93 | 104 | 115 | 126 |
| 0.18% | 6 | 17 | 28 | 39 | 50 | 61 | 72 | 83 | 94 | 105 | 116 | 127 |
| 0.20% | 7 | 18 | 29 | 40 | 51 | 62 | 73 | 84 | 95 | 106 | 117 | 128 |
| 0.23% | 8 | 19 | 30 | 41 | 52 | 63 | 74 | 85 | 96 | 107 | 118 | 129 |
| 0.25% | 9 | 20 | 31 | 42 | 53 | 64 | 75 | 86 | 97 | 108 | 119 | 130 |
| 0.28% | 10 | 21 | 32 | 43 | 54 | 65 | 76 | 87 | 98 | 109 | 120 | 131 |
| 0.30% | 11 | 22 | 33 | 44 | 55 | 66 | 77 | 88 | 99 | 110 | 121 | 132 |

| Tazarotene | Dapsone (w/w) | | | | | | | | | |
|---|---|---|---|---|---|---|---|---|---|---|
| (w/w) | 6.50% | 7.00% | 7.50% | 8.00% | 8.50% | 8.75% | 9.00% | 9.25% | 9.50% | 9.75% | 10.00% |
| 0.05% | 133 | 144 | 155 | 166 | 177 | 188 | 199 | 210 | 221 | 232 | 243 |
| 0.08% | 134 | 145 | 156 | 167 | 178 | 189 | 200 | 211 | 222 | 233 | 244 |
| 0.10% | 135 | 146 | 157 | 168 | 179 | 190 | 201 | 212 | 223 | 234 | 245 |
| 0.13% | 136 | 147 | 158 | 169 | 180 | 191 | 202 | 213 | 224 | 235 | 246 |
| 0.15% | 137 | 148 | 159 | 170 | 181 | 192 | 203 | 214 | 225 | 236 | 247 |
| 0.18% | 138 | 149 | 160 | 171 | 182 | 193 | 204 | 215 | 226 | 237 | 248 |
| 0.20% | 139 | 150 | 161 | 172 | 183 | 194 | 205 | 216 | 227 | 238 | 249 |

TABLE 1-continued

EFFECTIVE AMOUNTS OF TAZAROTENE AND DAPSONE

| 0.23% | 140 | 151 | 162 | 173 | 184 | 195 | 206 | 217 | 228 | 239 | 250 |
| 0.25% | 141 | 152 | 163 | 174 | 185 | 196 | 207 | 218 | 229 | 240 | 251 |
| 0.28% | 142 | 153 | 164 | 175 | 186 | 197 | 208 | 219 | 230 | 241 | 252 |
| 0.30% | 143 | 154 | 165 | 176 | 187 | 198 | 209 | 220 | 231 | 242 | 253 |

TABLE 2

EFFECTIVE AMOUNTS OF BENZOYL PEROXIDE AND CLINDAMYCIN

| Clindamycin (w/w) | Benzoyl peroxide (w/w) | | | | | | | | | | |
|---|---|---|---|---|---|---|---|---|---|---|---|
| | 0% | 0.50% | 1.00% | 1.50% | 2.00% | 2.50% | 3.00% | 3.50% | 4.00% | 4.50% | 5.00% | 5.50% |
| 0% | | 1012 | 1024 | 1036 | 1048 | 1060 | 1072 | 1084 | 1096 | 1108 | 1120 | 1132 |
| 0.50% | 1001 | 1013 | 1025 | 1037 | 1049 | 1061 | 1073 | 1085 | 1097 | 1109 | 1121 | 1133 |
| 0.75% | 1002 | 1014 | 1026 | 1038 | 1050 | 1062 | 1074 | 1086 | 1098 | 1110 | 1122 | 1134 |
| 1.00% | 1003 | 1015 | 1027 | 1039 | 1051 | 1063 | 1075 | 1087 | 1099 | 1111 | 1123 | 1135 |
| 1.25% | 1004 | 1016 | 1028 | 1040 | 1052 | 1064 | 1076 | 1088 | 1100 | 1112 | 1124 | 1136 |
| 1.50% | 1005 | 1017 | 1029 | 1041 | 1053 | 1065 | 1077 | 1089 | 1101 | 1113 | 1125 | 1137 |
| 1.75% | 1006 | 1018 | 1030 | 1042 | 1054 | 1066 | 1078 | 1090 | 1102 | 1114 | 1126 | 1138 |
| 2.00% | 1007 | 1019 | 1031 | 1043 | 1055 | 1067 | 1079 | 1091 | 1103 | 1115 | 1127 | 1139 |
| 2.25% | 1008 | 1020 | 1032 | 1044 | 1056 | 1068 | 1080 | 1092 | 1104 | 1116 | 1128 | 1140 |
| 2.50% | 1009 | 1021 | 1033 | 1045 | 1057 | 1069 | 1081 | 1093 | 1105 | 1117 | 1129 | 1141 |
| 2.75% | 1010 | 1022 | 1034 | 1046 | 1058 | 1070 | 1082 | 1094 | 1106 | 1118 | 1130 | 1142 |
| 3.00% | 1011 | 1023 | 1035 | 1047 | 1059 | 1071 | 1083 | 1095 | 1107 | 1119 | 1131 | 1143 |

| Clindamycin (w/w) | Benzoyl peroxide (w/w) | | | | | | | | | | |
|---|---|---|---|---|---|---|---|---|---|---|---|
| | 6.00% | 6.50% | 7.00% | 7.50% | 8.00% | 8.50% | 8.75% | 9.00% | 9.25% | 9.50% | 9.75% | 10.00% |
| 0% | 1144 | 1156 | 1168 | 1180 | 1192 | 1204 | 1216 | 1228 | 1240 | 1252 | 1264 | 1276 |
| 0.50% | 1145 | 1157 | 1169 | 1181 | 1193 | 1205 | 1217 | 1229 | 1241 | 1253 | 1265 | 1277 |
| 0.75% | 1146 | 1158 | 1170 | 1182 | 1194 | 1206 | 1218 | 1230 | 1242 | 1254 | 1266 | 1278 |
| 1.00% | 1147 | 1159 | 1171 | 1183 | 1195 | 1207 | 1219 | 1231 | 1243 | 1255 | 1267 | 1279 |
| 1.25% | 1148 | 1160 | 1172 | 1184 | 1196 | 1208 | 1220 | 1232 | 1244 | 1256 | 1268 | 1280 |
| 1.50% | 1149 | 1161 | 1173 | 1185 | 1197 | 1209 | 1221 | 1233 | 1245 | 1257 | 1269 | 1281 |
| 1.75% | 1150 | 1162 | 1174 | 1186 | 1198 | 1210 | 1222 | 1234 | 1246 | 1258 | 1270 | 1282 |
| 2.00% | 1151 | 1163 | 1175 | 1187 | 1199 | 1211 | 1223 | 1235 | 1247 | 1259 | 1271 | 1283 |
| 2.25% | 1152 | 1164 | 1176 | 1188 | 1200 | 1212 | 1224 | 1236 | 1248 | 1260 | 1272 | 1284 |
| 2.50% | 1153 | 1165 | 1177 | 1189 | 1201 | 1213 | 1225 | 1237 | 1249 | 1261 | 1273 | 1285 |
| 2.75% | 1154 | 1166 | 1178 | 1190 | 1202 | 1214 | 1226 | 1238 | 1250 | 1262 | 1274 | 1286 |
| 3.00% | 1155 | 1167 | 1179 | 1191 | 1203 | 1215 | 1227 | 1239 | 1251 | 1263 | 1275 | 1287 |

EXAMPLES

Embodiments of the present invention are further illustrated by the following examples, which are not to be construed in any way as imposing limitations upon the scope thereof. On the contrary, it is to be clearly understood that resort may be had to various other embodiments, modifications and equivalents, which, after reading the description provided herein, may suggest themselves to those skilled in the art without departing from the spirit of the invention.

Example 1

Topical combination compositions described herein are prepared according to conventional processes and tested in the clinical studies. A clinical study is conducted by forming a treatment group and a control group of patients having acne. The treatment group is subjected to the application of a topical combination composition being tested, comprising tazarotene and one or more no-retinoid topically active ingredients. Application can be conducted once or twice daily. A control group is subjected to the application, at the same frequency as the treatment group, of a control composition comprising the same excipients and concentration of tazarotene as the topical combination composition, but no non-retinoid topically active ingredients. The patients' inflammatory and non-inflammatory acne lesion counts are recorded at baseline before initiation of treatment and then at select intervals throughout the study. The reduction in total, non-inflammatory or inflammatory lesions counts provides determination of the efficacy of the formulations. The established Global Acne Assessment Score (GAAS) is used to assess efficacy of the product. The tolerability of the product is also determined by assessment of skin dryness, irritation, sensitivity and redness as a result of treatment.

Example 2

Two separate 12-week clinical studies evaluated the combination of tazarotene with either clindamycin/benzoyl peroxide or dapsone in comparison with tazarotene monotherapy. Patients treated with a gel containing clindamycin at 1% w/w and benzoyl peroxide at 5% w/w in combination with s cream containing 0.1% tazarotene w/w ("tazarotene cream") (n=60) achieved a statistically significant reduction of 68% in comedonal lesion count at week 12 in comparison with a 48% reduction achieved by patients treated only with tazarotene cream (n=61; P=0.0124). Patients treated with a gel containing dapsone at 5% w/w in combination with tazarotene cream achieved a 60% reduction in comedonal lesion count at week 12, in comparison with a reduction of 47% observed for the tazarotene monotherapy patients (n=85; P=0.0097). The combination of topical tazarotene with a topical anti-inflammatory agent or a fixed-dose combination benzoyl peroxide/clindamycin product exhibited unexpectedly high efficacy in patients with comedonal acne.

What is claimed is:

1. A method of alleviating, reducing, or inhibiting acne in a patient in need thereof, said method consisting of administering to said patient a topical pharmaceutical composition comprising 0.1% w/w tazarotene and 5% w/w dapsone, wherein the topical pharmaceutical composition is a cream.

2. The method of claim 1, wherein said acne is acne vulgaris.

3. The method of claim 1, wherein said acne is comedonal acne.

4. A method of alleviating, reducing, or inhibiting comedonal acne in a patient in need thereof, said method comprising administering to said patient a topical pharmaceutical composition consisting of 0.1% w/w tazarotene and 5% w/w dapsone, wherein the topical pharmaceutical composition is a cream wherein the method results in a 60% reduction in comedonal lesion count at week 12, in comparison with a reduction of 47% for a patient who has undergone 0.1% w/w tazarotene monotherapy.

* * * * *